(12) United States Patent
Stewart

(10) Patent No.: US 6,840,091 B1
(45) Date of Patent: Jan. 11, 2005

(54) GEOPHYSICAL METHOD FOR QUANTIFICATION OF DENSE NON-AQUEOUS PHASE LIQUIDS IN THE SUBSURFACE

(75) Inventor: Mark T. Stewart, Lutz, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 10/604,240

(22) Filed: Jul. 3, 2003

Related U.S. Application Data

(60) Provisional application No. 60/319,380, filed on Jul. 5, 2002.

(51) Int. Cl.$^7$ ............................................. E21B 49/08
(52) U.S. Cl. ................. 73/53.01; 73/152.18; 73/152.42
(58) Field of Search .......................... 73/53.01, 152.18, 73/152.42

(56) References Cited

U.S. PATENT DOCUMENTS

| | | | | |
|---|---|---|---|---|
| 4,654,598 A | * | 3/1987 | Arulanandan et al. ...... | 324/354 |
| 5,319,966 A | * | 6/1994 | Jackson et al. .......... | 73/152.23 |
| 6,003,365 A | | 12/1999 | Pope et al. ............. | 73/152.39 |

OTHER PUBLICATIONS

The Neutron Log; www.logwell.com/tech/nuclear/neutron_log.html; May 20, 2003.

The Gamma Ray Log; www.logwell.com/tech/nuclear/gamma_ray_log.html; May 20, 2003.

Kram et al.; DNAPL Characterization Methods and Approaches Part1: Performance Comparisions, (no date).

Shinn et al.; Development of a CPT Deployed Probe for In Situ Measurement of Volumetric Soil Moisture Content and Electrical Resistivity; Dec. 31, 1997.

Innovative Technology Summary Cone Penetrometer; www.gnet.org/archive/4569.html; May 21, 2003.

Stewart; A Geophysical Method for Quantification of Dense Non–Aqueous Phase Liquids (DNAPL) in the Subsurface, (no date).

Direct Push Technologies, (no date).

Bulk Density Determination; www.geology.iupui.edu/research/SoilsLab/procedures/bulk/; May 19, 2003.

* cited by examiner

*Primary Examiner*—Daniel S. Larkin
(74) *Attorney, Agent, or Firm*—Molly L. Sauter; Smith & Hopen, P.A.

(57) ABSTRACT

The present invention is a method of calculating non-aqueous phase liquid saturation in a soil sample including the steps of measuring the bulk dielectric constant of the sample, measuring the bulk density of the sample, estimating the bulk porosity of the sample from the measured bulk density and calculating the non-aqueous phase liquid saturation from the measured bulk dielectric constant and the estimated bulk porosity.

9 Claims, 14 Drawing Sheets

Fig. 1

Dielectric Constants of Selected Materials.

| Material | Dielectric Constant |
|----------|---------------------|
| Air | 1.0 |
| Quartz | 3.4 |
| Water | 80 |
| TCE | 3.390 |
| PCE | 2.268 |

(From Or et al., 1998; CRC, 2000).

Fig. 2

$$\Phi = \frac{\rho_{ma} - \rho_b}{\rho_{ma} - \rho_f}$$

where:

$\Phi$ = porosity $\rho_{ma}$ = matrix density (2.65 g/cm$^3$, quartz)

$\rho_b$ = formation bulk density $\rho_f$ = average density of pore fluid (1.00 g/cm$^3$, water)

Fig. 3

$$\rho_b = (1-\Phi)\rho_{ma} + \Phi \ast \rho_f$$

where:

$\Phi$ = porosity $\rho_{ma}$ = matrix density (2.65 g/cm$^3$, quartz)

$\rho_b$ = formation bulk density $\rho_f$ = average density of pore fluid (1.00 g/cm$^3$, water; 1.4 g/cm$^3$, DNAPL)

Fig. 4

0% DNAPL:  $\rho_b = (0.8)*(2.6) + (0.2)*(1) = 2.28$ g/cm$^3$

50% DNAPL: $\rho_b = (0.8)*(2.6) + (0.1)*(1) + (0.1)*(1.4) = 2.32$ g/cm$^3$

100% DNAPL: $\rho_b = (0.8)*(2.6) + (0.2)*(1.4) = 2.36$ g/cm$^3$

Fig. 5

% change = $\frac{(2.36-2.28)}{2.28}$ = .035 * 100% ≅ 4% change in bulk density

Fig. 6

$$\varepsilon_b = [\theta v * \varepsilon_w^\beta + (1-\eta)\varepsilon_s^\beta + (\eta-\theta v)\varepsilon_c^\beta]^{1/\beta}$$

where:

| | |
|---|---|
| $\varepsilon_b$ | = bulk dielectric |
| $\theta v$ | = fractional fluid volume |
| $\varepsilon_w$ | = water dielectric |
| $\varepsilon_s$ | = soil dielectric |
| $\varepsilon_c$ | = DNAPL dielectric |
| $\eta$ | = porosity |
| $\beta$ | = constant, usually 0.5 |

Fig. 8

Selected DPT results for dissolved TCE in vicinity of study area, (concentrations in µg/L).

| elev. depth | -2 ft 10 ft | -7 ft 15 ft | -12 ft 20 ft | -17 ft 25 ft | -22 ft 30 ft | -27 ft 35 ft | -32 ft 40 ft | -37 ft 45 ft | -42 ft 50 ft |
|---|---|---|---|---|---|---|---|---|---|
| DPT 05 | 53,000 | 382,000 | 238,000 | 97,000 | 87,500 | 16,800 | 1000 | | |
| DPT 07 | 1,260 | 189,000 | 1,050,000 | 608,000 | 4,400 | 10,200 | 7,500 | | |
| DPT 29 | 23,300 | 261,000 | 18,600 | 51,200 | 732 | 33.2 | 1,860 | | |
| DPT 34 | 5,200 | 52,800 | 961,000 | 192,000 | 2,200 | 889,000 | 169,000 | | |
| DPT 16 | 4,330 | 1,370,000 | 532,000 | 352,000 | 257,000 | 112,000 | 105,000 | 165,000 | 2,170 |
| DPT 54 | 1,550 | 676,000 (-6 ft) | 958,000 (-10 ft) | 47,000 | 9,100 | 12,600 | 1,060 | 955 | 2,750 |
| DPT 16 | 1.0 U | | 1.0 U | | 1.0 U | | 1.0 U | | |

Where: U = analyte analyzed for but not detected at corresponding detection limit Figure 10. DNAPL saturation versus elevation.

GEOPHYSICAL METHOD FOR QUANTIFICATION OF DENSE NON-AQUEOUS PHASE LIQUIDS IN THE SUBSURFACE

CROSS REFERENCE TO RELATED APPLICATIONS

This disclosure claims the benefit of provisional patent application Ser. No. 60/319,380, filed on Jul. 5, 2002.

BACKGROUND OF INVENTION

1. Field of Invention

This invention relates to the quantification of contaminants in soil and more particularly to a geophysical method for quantifying the volume of dense non-aqueous phase liquids in the subsurface.

2. Background of the Invention

Dense non-aqueous phase liquids (DNAPL) are common and highly problematic contaminants of concern in ground water. They are of concern at dissolved concentrations orders of magnitude lower than their solubility, they can migrate many meters vertically in soils within hours or days, they pool at horizontal porosity and permeability boundaries, and their migration is little effected by groundwater flow or gradients.

Quantifying the volume of non-aqueous phase liquids in the subsurface is difficult. To date, methods have been developed which can detect DNAPL in the subsurface but these methods are not effective in quantifying the amount of DNAPL present. As cleanup costs at DNAPL sites typically run in the millions of dollars, accurately quantifying the volume of DNAPL present is very important. There is a need for a method to locate and quantify the extent of organic contaminants in the non-aqueous phase in order to develop strategies to remediate the DNAPL sources. Site remediation is dependent upon reducing a certain percentage of the DNAPL contaminant mass that is the source for the dissolved contaminant plume. In order to estimate the amount of mass that needs to be removed, the percent saturation of DNAPL within the subsurface needs to be reasonably quantified.

Accordingly, what is needed in the art is a method that can directly detect and quantify the volume of DNAPL present in a saturated soil.

It is, therefore, to the effective resolution of the aforementioned problems and shortcomings of the prior art that the present invention is directed.

However, in view of the prior art in at the time the present invention was made, it was not obvious to those of ordinary skill in the pertinent art how the identified needs could be fulfilled.

SUMMARY OF INVENTION

The present invention is a method of detecting and quantifying non-aqueous phase liquids in a soil sample. In a preferred embodiment, the method includes the steps of measuring the bulk dielectric constant of the sample, measuring the bulk density of the sample, estimating the bulk porosity of the sample from the measured bulk density, and calculating the non-aqueous phase liquid saturation from the measured bulk dielectric constant and the estimated bulk porosity.

In an additional embodiment, 100% water saturation and a matrix density 2.65 g/cc are assumed when estimating the bulk porosity from the bulk density measurements of the sample.

In another embodiment, the non-aqueous phase liquid is a dense non-aqueous phase liquid.

In yet another embodiment, the soil sample is in the subsurface. The steps of measuring the bulk dielectric constant and measuring the bulk density are performed in situ and the bulk dielectric constant of the subsurface is measured at a plurality of depths and bulk porosity of the subsurface is measured at the same plurality of depths and the bulk dielectric constant measurements at the plurality of depths and the bulk porosity measurements at the same plurality of depths are used to calculate the non-aqueous phase liquid saturation at the plurality of depths.

In a preferred embodiment of the present invention, the sample is in the subsurface and the measurements are performed in situ, whereby a logging well and an active gamma logging tool are provided to measure the bulk density of the subsurface at a plurality of vertical intervals along the length of the logging well. A cone-penetrometer tool (CPT) is provided having dielectric constant measurement capability. The CPT is used to measure the dielectric constant of the subsurface at a second plurality of vertical intervals. The bulk density measurements and the dielectric constant measurements are interpolated to establish a series of measurements at a plurality of consistent vertical intervals. The bulk porosity of the subsurface at the plurality of consistent vertical intervals is then estimated from the interpolated bulk density, assuming 100% water saturation and a matrix density of 2.65 g/cc. The percent non-aqueous phase liquid saturation is then determined at the plurality of consistent vertical intervals from the interpolated dielectric constant and the interpolated bulk porosity.

In yet another embodiment, a cone-penetrometer tool is provided. The cone-penetrometer tool includes a bulk density measurement device and a dielectric constant measurement device. With the bulk density measurement device and the dielectric constant measurement device existing on the cone-penetrometer tool the bulk density measurements and the dielectric constant measurements of the subsurface can be obtained simultaneously at a plurality of vertical intervals within the subsurface. Interpolation is not necessary and the measurements can be used to estimate the bulk porosity of the subsurface and for the subsequent calculation of the percent non-aqueous liquid saturation of the subsurface at the plurality of vertical intervals.

It is to be understood that both the foregoing general description and the following detailed description are explanatory and are not restrictive of the invention as claimed. The accompanying drawings, which are incorporated in and constitute part of the specification, illustrate embodiments of the present invention and together with the general description, serve to explain principles of the present invention.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF DRAWINGS

For a fuller understanding of the nature and objects of the invention, reference should be made to the following detailed description, taken in connection with the accompanying drawings, in which:

FIG. 1 is a table of dielectric constants for selected materials.

FIG. 2 is an equation used to calculate the porosity assuming 100% water saturation from the results of the bulk density measurements.

FIG. 3 is an equation used to calculate formation bulk density from porosity, the matrix density of quartz and the average density of pore fluid.

FIG. 4 illustrates the results of the bulk density calculations using the equation of FIG. 3.

FIG. 5 is an equation used to calculate the percentage of change in bulk density over a 100% change in DNAPL saturation.

FIG. 6 is an equation used to calculate bulk dielectric.

FIG. 8 shows dielectric response to porosity.

DETAILED DESCRIPTION

Figure 7:
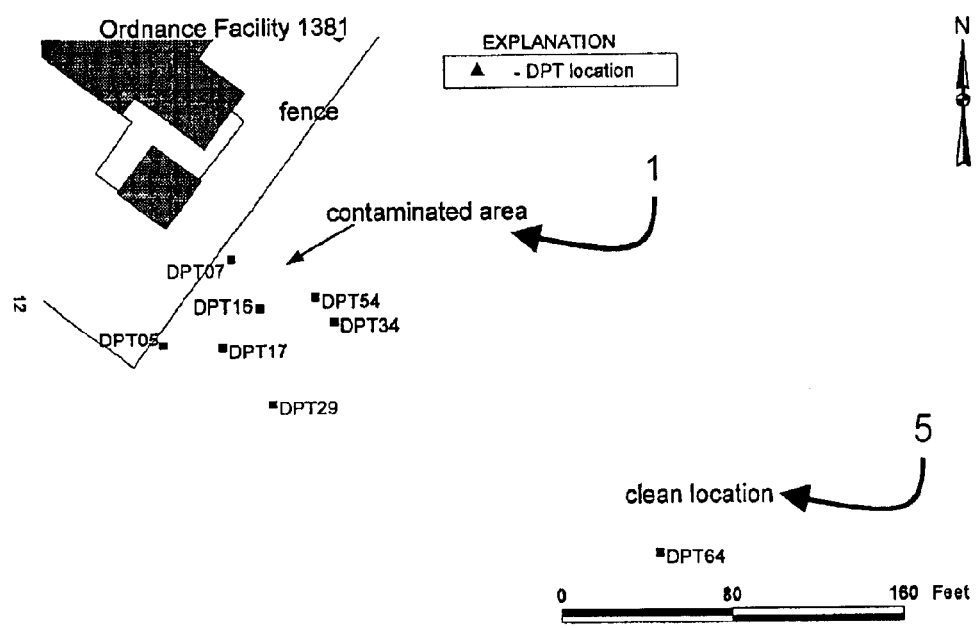
FIG. 7 is an equation showing the relationship between chlorine concentration and the court rate for chlorine.

The present invention utilizes the measurements of the bulk dielectric and the bulk density of the subsurface to detect and quantify the volume of DNAPL present at a sample point.

The dielectric constant of a medium is the ratio squared of the electromagnetic propagation velocity in a vacuum relative to the velocity in that medium. The variables which can affect this electrical property include soil texture, water content and density. The dielectric constant values that can be used to identify materials in the subsurface are presented as shown in FIG. 1. It is known that DNAPLs have very low dielectric constant values (3–4) compared with water (80). Because the dielectric values vary greatly between water and DNAPL, displacement of pore water with DNAPL significantly changes the measured value of the balk dielectric constant. Replacing water in pore spaces with DNAPL will cause a decrease in the dielectric constant.

An electronic piezocone (cone penetrometer, or CPT) is used to provide hydrogeologic profiling for environmental and geotechnical projects. The CPT provides a rapid, reliable and economical means of determining soil stratigraphy, relative density, strength and hydrogeologic information in contaminated soils, without generating contaminated waste cuttings. The present invention utilizes an electronic piezocone or cone penetration test (CPT) to measure variations in dielectric constant with depth. The CPT is employed along with stratigraphy and bulk resistivity. The numbers of CPT holes are chosen to cover as much of the area extent of the suspected source area as possible and to penetrate at least to the top of the first significant low permeability layer. The spatial arrangement of the CPT holes within the area is based on site layout and accessibility for both the CPT equipment and drilling rigs. Gamma-gamma logging, or bulk density, logging is employed to measure the bulk density of the sample. An active gamma source generates high energy gamma radiation, some of which is reflected back to the logging tool by the surrounding soil. The amount of backscattered gamma radiation is proportional to the bulk density of the soil. The gamma-gamma logging is performed in monitoring wells, which are preferred to be next to a CPT hole. Current technology requires density logging in boreholes adjacent to the CPT locations, but the dielectric and density logging tools could be placed on the CPT tool, eliminating the need for the boreholes.

It is known that the dielectric constant varies with both porosity and DNAPL saturation. A decrease in porosity will also cause a decrease in the dielectric constant, so to use the dielectric constant to quantify the volume of DNAPL present; it is necessary to also measure porosity. The present invention addresses this problem by using the gamma-gamma log. In order for this solution to be feasible, the CPT holes need to be located next to monitoring wells that will be used for the gamma-gamma logging. The gamma-gamma log uses a sonde that is lowered within the borehole until it is in contact with the formation wall or well bore. A gamma-ray source attached to the probe emits gamma rays that pass into the formation and bombard the electrons within the formation. Gamma rays that are scattered back to the detectors are counted and used to calculate the bulk density. Using the known densities of water and quartz, porosity can be calculated from bulk density. Once variations in porosity are identified, variations in dielectric constant can be correlated to changes in DNAPL. The results of the bulk density measurements are used to calculate the porosity assuming 100% water saturation. This equation is provided in FIG. 2.

A complication encountered is that the presence of DNAPL changes the bulk density, and assuming 100% water saturation leads to an error in the calculation of porosity. However, the effect of DNAPL on bulk density is much less than on the bulk dielectric. The percent difference in bulk density values from variations in DNAPL saturation is very small and can be illustrated using the equation of FIG. 3, assuming 100% pore saturation. As an example, using the equation of FIG. 3, an estimated porosity of 0.2, and percentages of DNAPL of 0%, 50% and 100%, the results for changes in bulk density are provided in FIG. 4. The percent change in bulk density (maximum change) over a 100% change in DNAPL saturation can be calculated as shown in FIG. 5. It has been shown that DNAPL can occupy 40–70% of the bulk pores space. If the maximum possible DNAPL saturation is approximately 70%, the percent error in calculating the bulk densities as a result of the presence of DNAPL will range from 0–2.8%.

In order to determine how the bulk dielectric will change with variations in DNAPL saturation, a mixing model equation is applied. This equation calculates bulk dielectric constant in a three-phase system assuming 100% pore saturation and is dependent upon, porosity, medium geometry, and the dielectric constants of water, soil and DNAPL. The equation used to calculate the bulk dielectric constant for a DNAPL, water, and soil system is obtained by substituting a term for DNAPL for the term for air in the mixing equation for a water, soil, and air system as provided in FIG. 6. Using the equation of FIG. 6, the bulk dielectric can be calculated using a range of porosity values for different percent DNAPL saturation values. For a porosity of 0.20, the bulk dielectric constant decreases by about 35% as the DNAPL saturation (% of available pore space) increases from 10% to 70%. These calculations illustrate that DNAPL saturation has a significant effect on the bulk dielectric. The bulk dielectric changes by 80% from varying percent DNAPL saturation from 0 to 100% DNAPL at a constant porosity. The percent change in bulk dielectric with varying porosity at three selected DNAPL saturation values ranges from 0 (porosity=0) to a maximum of 219 (porosity=0.7). There is a direct relationship between bulk dielectric and porosity while there is an inverse relationship between bulk dielectric and percent DNAPL saturation.

The previous calculations with respect to the equation of FIG. 3, demonstrate the small effect that DNAPL saturation has on bulk density values. The range in percent differences of bulk density values were from 0–2.8% over a range of percent DNAPL saturation values from 0–70%. The presence of DNAPL will not change the bulk density significantly enough to have a noticeable effect on the estimated porosity. Therefore the estimated porosity obtained from the gamma-gamma log results can be used in FIG. 6 with the bulk dielectric values to determine the DNAPL saturation.

The fractional DNAPL volume was calculated using the equation of FIG. 6, the observed bulk dielectric constant, porosity, and the dielectric constants for water, quartz sand, and DNAPL. The dissolved phase constituents of the sample are used to determine the dielectric constant for DNAPL. Porosity, water content and DNAPL content are expressed as fractional volumes, which are the volume of the pores, the water or the DNAPL divided by the total volume. DNAPL saturation refers to the percentage of available pore space occupied by DNAPL. For example, a fractional DNAPL volume of 0.20 in a soil with a porosity of 0.40 yields a DNAPL saturation of 50%.

The present invention provides a non-intrusive, quantifiable and defensible calculation of the percent of DNAPL saturation within the subsurface. Applied spatially, the results can be used to estimate the amount of DNAPL mass present in the subsurface and could be used in a mass transport model to predict how the dissolved plume will change over time based upon a certain percentage of mass removal. Knowledge of the amount of DNAPL present will also aid in choosing the appropriate remediation technology. The practice can be applied at DNAPL contaminated sites and a gamma-gamma logging tool could be installed with the CPT and resistivity probe to combine the technologies, thus eliminating the dependence on monitoring wells and the costs associated with their installation.

The following example is provided as exemplary of the method of the present invention and is not intended to limit the scope of the inventions or claims thereto.

The method of the present invention was employed for the quantification of DNAPL in saturated soils at a test site known to be heavily contaminated with DNAPL, principally TCE and DCE. The site was located on a large barrier island complex in the Southeastern U.S. The presence of DNAPL was confirmed by water-quality sampling using direct push tools to define the study area as shown in FIG. 7 where the contaminated areas 1 and clear locations 5 are identified. High concentrations, greater than 100,000 $\mu$g/l, of dissolved phase TCE occur at the site as shown in the table of FIG. 8. Dissolved concentrations in excess of 1% of saturation are considered to indicate the presence of residual DNAPL.

The general site stratigraphy consists of marine sands and silts with some clay. Land surface elevations are about 5 to 8 ft above sea level (msl). Clean, well-sorted sands are present from the surface to elevations of 0 to +2 ft msl. Three or four silty layers a few feet thick each are present in the upper 35 to 40 ft, and a persistent clayey, silty sand at elevations of 40 to 45 ft msl forms the bottom of the upper surficial aquifer. The water table is at an elevation of about +2 ft msl under the site.

The original source of the DNAPL, and the amounts disposed of, are not known, but the dissolved concentrations suggest that the residual DNAPL is confined to a roughly oval area about 100 ft wide and 200 ft long. Highest dissolved TCE concentrations are found between elevations of 7 to 22 ft msl, with concentrations generally falling below 100,000 $\mu$g/l at elevations below 30 to 35 ft msl.

Figure 9:
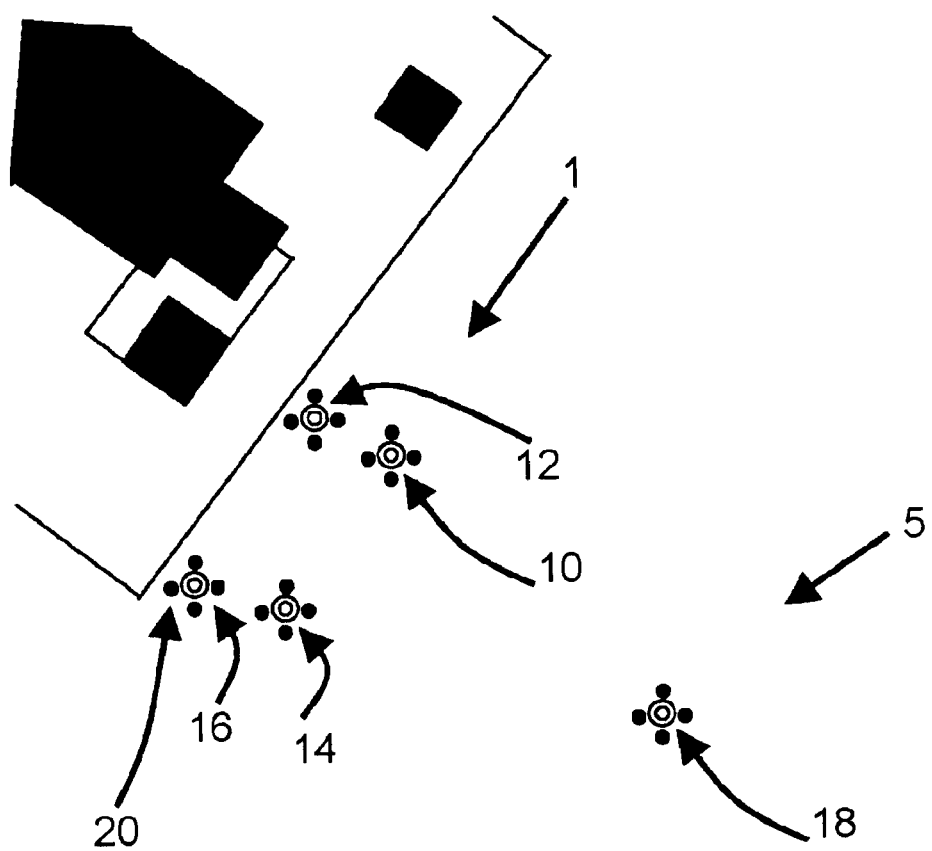
FIG. 9 shows dielectric response to DNAPL.

Five wells were constructed to obtain the borehole logs. The wells were drilled using the rotosonic method to minimize soil disturbance. The wells were cased with 3 inch inside diameter PVC casing to minimize the annular space between the casing and the in-hole tools. All five wells were cased to 50 ft below land surface, or an elevation of about 42 ft. This places the bottom of each well several feet below the top of the persistent lower permeability layer that forms the bottom of the upper surficial aquifer and apparently restricts vertical movement of DNAPL. As shown in FIG. 9, four wells, identified as 10, 12, 14 and 16, were completed within the heavily contaminated area 1 and a "clean" well, 18, was completed at the clean location 5.

Each well was logged four times with an active gamma (density) tool, a natural gamma tool, and a neutron (porosity) logging tool. The active gamma tool utilizes two detectors to allow correction for near-hole disturbance. The effect of the PVC casing was removed during data processing by calibrating the tool with a piece of the casing used to construct the wells. The vertical resolution of the active gamma tool is about 3–8 inches.

The tool for measuring the dielectric constant was mounted on a cone-penetrometer tool string (CPT) and pushed into the ground with a hydraulic ram. The CPT locations were placed as close to the wells as possible. The CPT locations are about 1–3 ft from the wells. Each well was surrounded by four CPT locations. The CPT locations are exemplified by element 20 shown in FIG. 9. The CPT tool recorded tip pressure, sleeve resistance, pore pressure, electrical resistivity, and dielectric constant.

The data from the CPT and geophysical logs were interpolated to consistent 0.1 ft vertical intervals, as variations in logging speeds created non-uniform vertical sampling intervals. A simple linear interpolation was made between data points and density and dielectric values were selected at corresponding depths at 0.1 ft intervals to calculate DNAPL volume.

Figure 10:
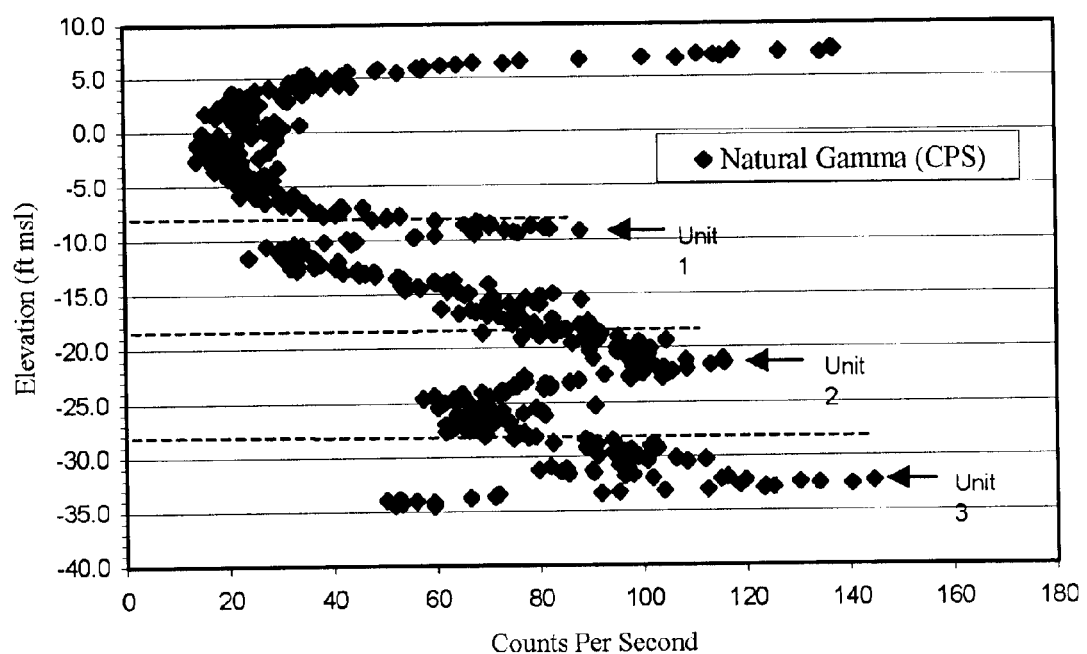
FIG. 10 illustrates the results of a natural gamma log used to determine the site stratigraphy.

The natural gamma logs were used to determine the site stratigraphy, as silts and clays are stronger gamma emitters than clean sands. Using the average of the four logging runs from well 16 as an example, the gamma stratigraphy suggests a general increase in silt/clay content with depth, and three prominent fine-grained layers at elevations of about 8 to −10 ft, −18 to 22 ft, and 29 to 33 ft, as shown in FIG. 10. The estimated tops of the layers are indicated on FIG. 10 by dashed lines and the centers of the fine-grained layers are indicated on FIG. 10 by arrows identifying Unit 1 at 9 ft, Unit 2 at 21 ft, and Unit 3 at 33 ft. Natural gamma logs from the other four wells show the same three principal fine-grained layers.

Figure 11:
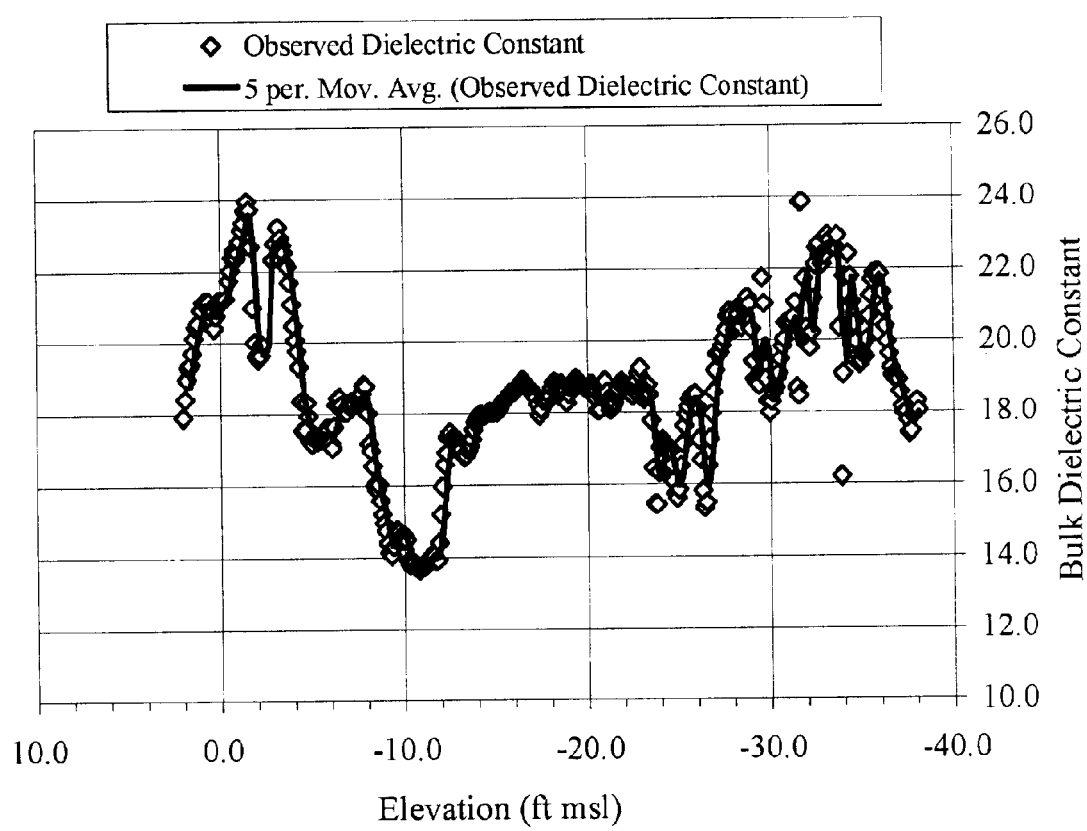
FIG. 11 is a graph illustrating the bulk dielectric constant relative to elevation of the site.
Figure 12:
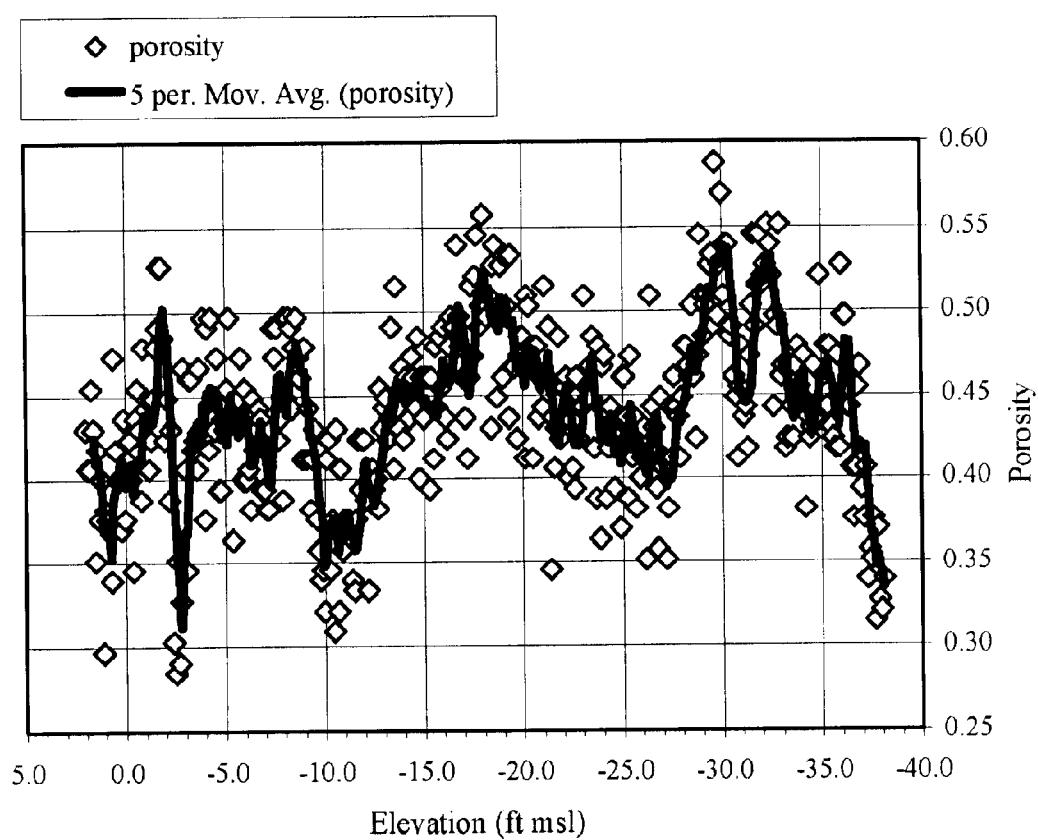
FIG. 12 is a graph illustrating the porosity relative to elevation of the site.

The values measured in the field were the bulk dielectric constant, $\epsilon_b$, and the bulk density. Porosity was calculated from bulk density by assuming 100% water saturation and a matrix density of 2.65 g/cc. Plots of $\epsilon_b$ versus elevation as shown in FIG. 11 and porosity versus elevation as shown in FIG. 12 for well 16 indicate that both the dielectric constant and porosity vary significantly with depth. Bulk dielectric constant values range from about 14 to 24, while porosity varies from about 0.3 to 0.55. A large, low value anomaly is apparent in both the porosity and $\epsilon_b$ data at about 11 ft. This corresponds to a very low natural gamma response at 11 ft, and is correlated with a clean, coarse sand. A high porosity, high $\epsilon_b$ response occurs at about 33 ft. This anomaly corresponds to the highest natural gamma counts in well 16, and correlates with a silty, clayey fine sand.

Figure 13:
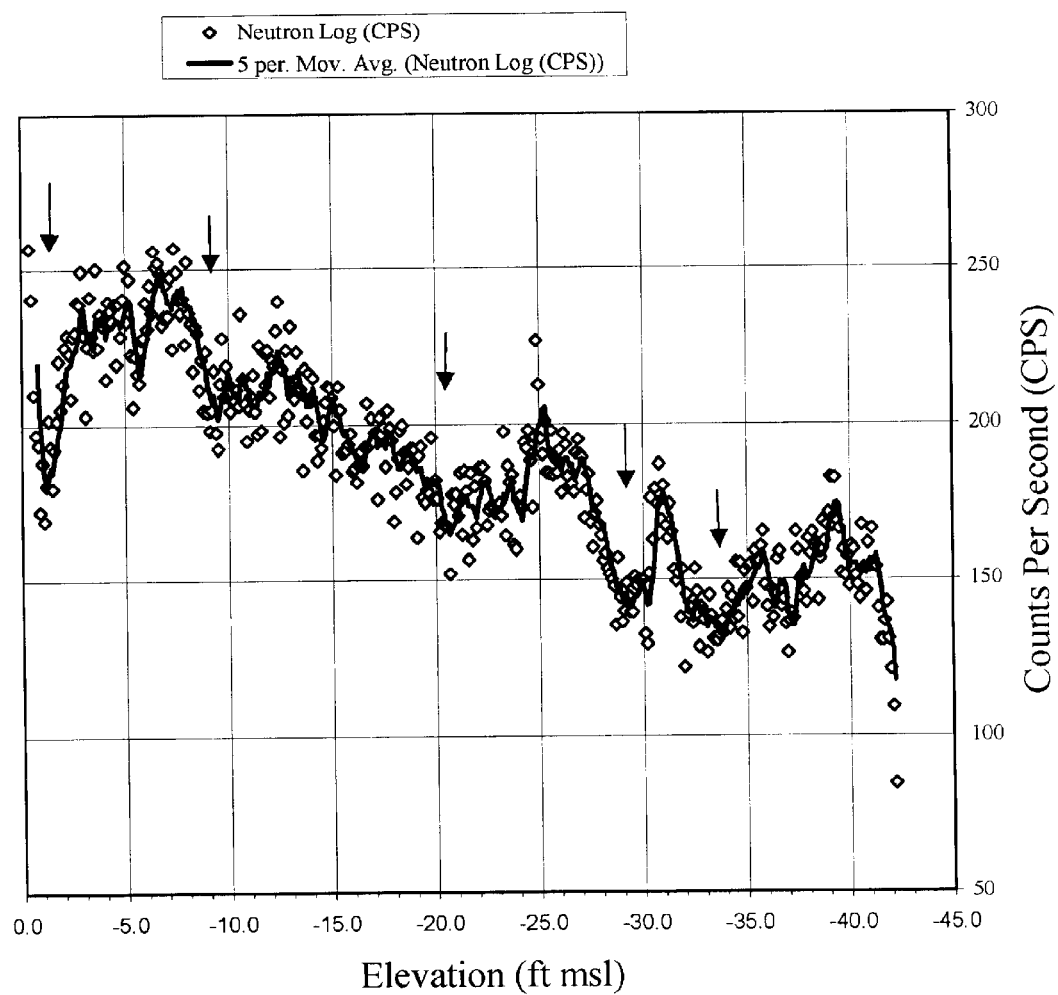
FIG. 13 is a graph illustrating the neutron log for the well.

The neutron log for well 16, as shown in FIG. 13, indicates a general decrease in counts per second with depth. There are several elevations where the CPS values are lower than elevations above or below. These are indicated on FIG. 13 by the arrows, and occur at 1 ft, −9 ft, −21 ft, −29 ft, and 33 ft.

Figure 14:
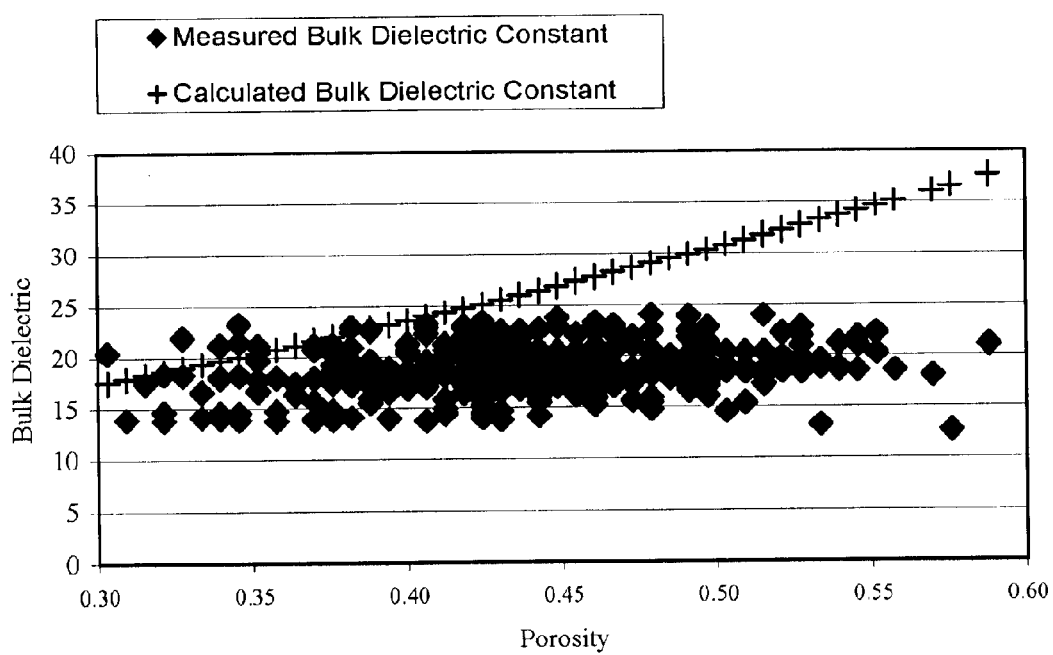
FIG. 14 illustrates the calculated dielectric constant relative to the field values of porosity.

The presence of DNAPL in pore spaces below the water table reduces the observed bulk dielectric constant from the value that would be obtained with no DNAPL present, for an observed porosity value. The value of the dielectric constant expected for a measured porosity value and 100% water saturation can be calculated from the equation shown in FIG. 6. The vertical displacement of the observed value of the dielectric constant from the calculated value is the result of the presence of DNAPL. FIG. 14 shows the dielectric constant calculated from Roth's equation, assuming 100% water saturation, from field values of porosity, and field measured values of the bulk dielectric constant. Porosity and dielectric data pairs are from the same elevations.

Figure 15:
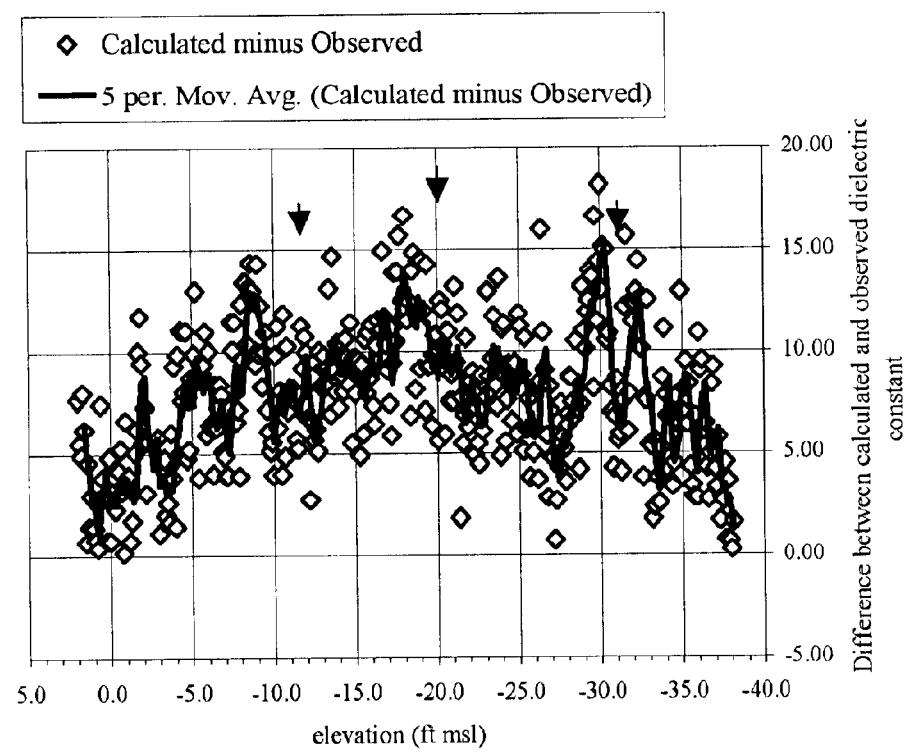
FIG. 15 illustrates the difference between the calculated and observed values of the dielectric constant.

The difference between the calculated and observed values of the dielectric constant, $\epsilon_b$ and $\epsilon_t$, is a qualitative measure of the presence of DNAPL. A plot of $\epsilon_b$-$\epsilon_t$ versus elevation, as shown in FIG. 15, gives a qualitative measure of the presence of DNAPL in the subsurface. The plot of calculated minus observed dielectric constant suggests three principal concentrations of residual DNAPL at elevations of 8 ft, −18 ft, and 30 ft. These elevations correspond to the estimated elevations of the tops of the lower permeability layers indicated by the natural gamma log at elevations of 9 ft, −21 ft, and 33 ft. These high natural gamma response layers have apparently caused the DNAPL to accumulate just above them.

Figure 16:
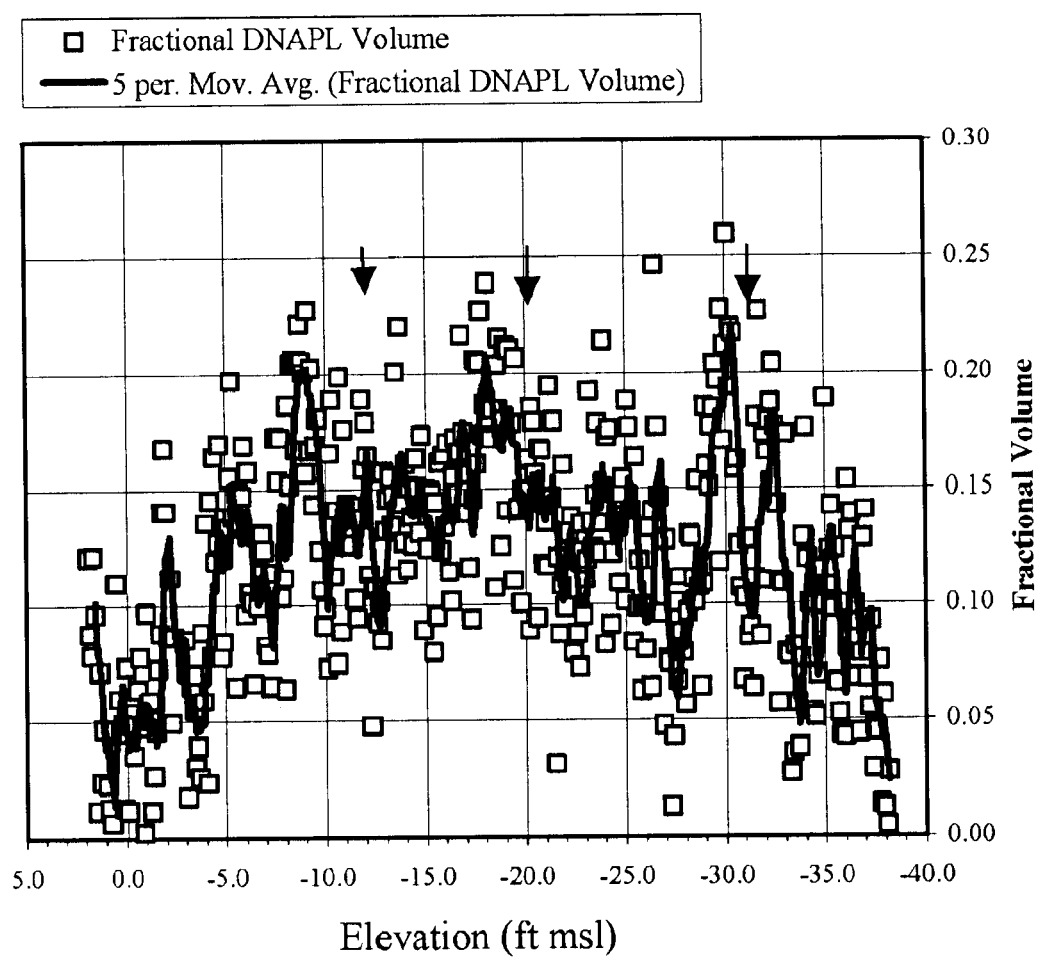
FIG. 16 illustrates the quantitative measure of the volume of DNAPL present as a fraction of the total volume.

The observed values of porosity and $\epsilon_b$ at each depth can be used to calculate the fractional DNAPL volume, $\epsilon_D$, using the equation of FIG. 6. This calculation gives a quantitative measure of the volume of DNAPL present as a fraction of the total volume as shown in FIG. 16. Again, the plot indicates three principal concentrations of DNAPL at elevations of 8.5 ft, −18 ft, and 30 ft. Fractional DNAPL volume at these three elevations is >0.20. DNAPL volumes are generally >0.10 between elevations of 5 to 35 ft.

Figure 17:
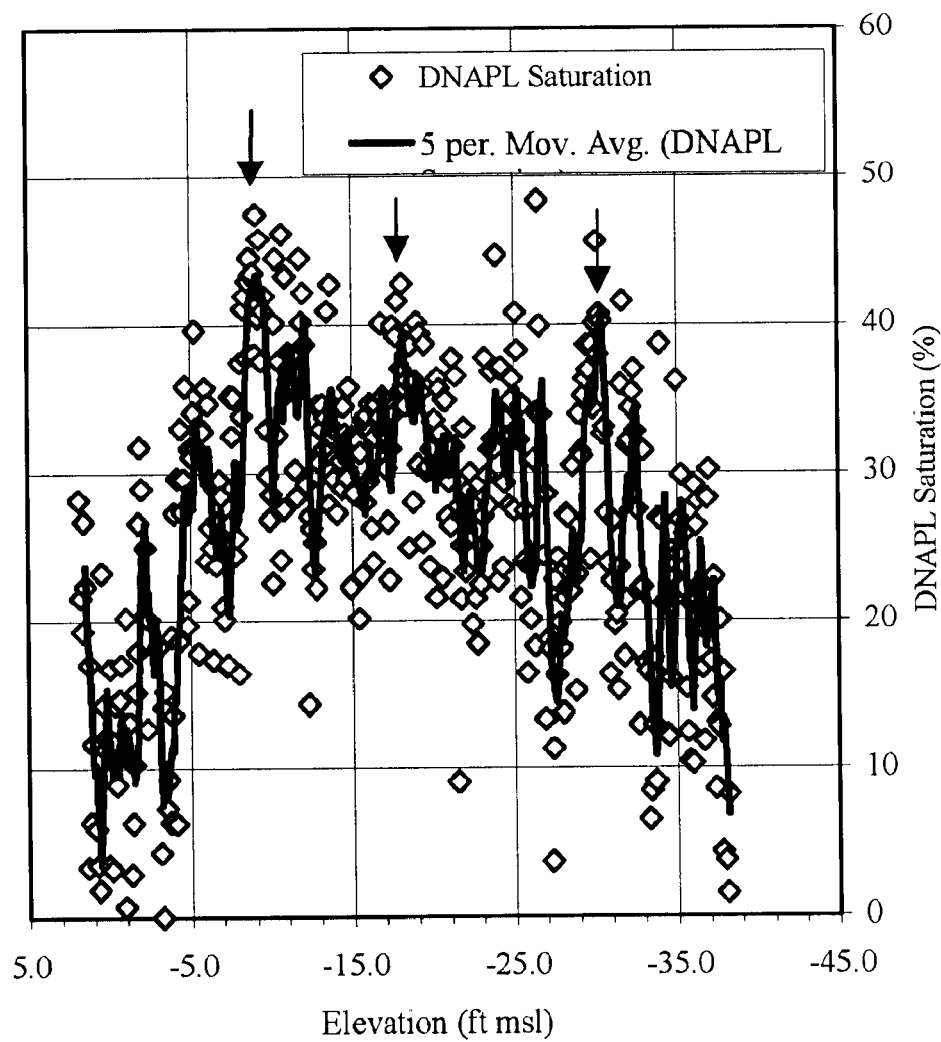
FIG. 17 is an illustrative plot of DNAPL saturation versus depth.

The DNAPL saturation is the relative volume of the available pore space occupied by DNAPL. It can be easily calculated by dividing the fractional DNAPL volume, $\epsilon_D$ by the porosity, $\theta_D$. Multiplying the ratio by 100 expresses DNAPL saturation as a percentage of available pore space. A plot of DNAPL saturation versus depth as shown in FIG. 17, shows the same three principal DNAPL peaks at 9, 18, and 30 ft. At these depths, DNAPL saturation is about 40–46%. Saturation is generally greater than 25% between elevations of 5 to 35 ft.

At any given depth, the range in fractional DNAPL is about +−0.05. The most serious source of noise is that the dielectric constant and active gamma tools did not pass through the same sediment column, as the CPT locations were a few feet away from the wells where the gamma logs were run. A CPT tool with both an active gamma instrument and the dielectric constant instrument would serve to eliminate much of the noise in the data, and would make vertical correlation of the dielectric constant and porosity measurements more accurate and precise.

Figure 18:
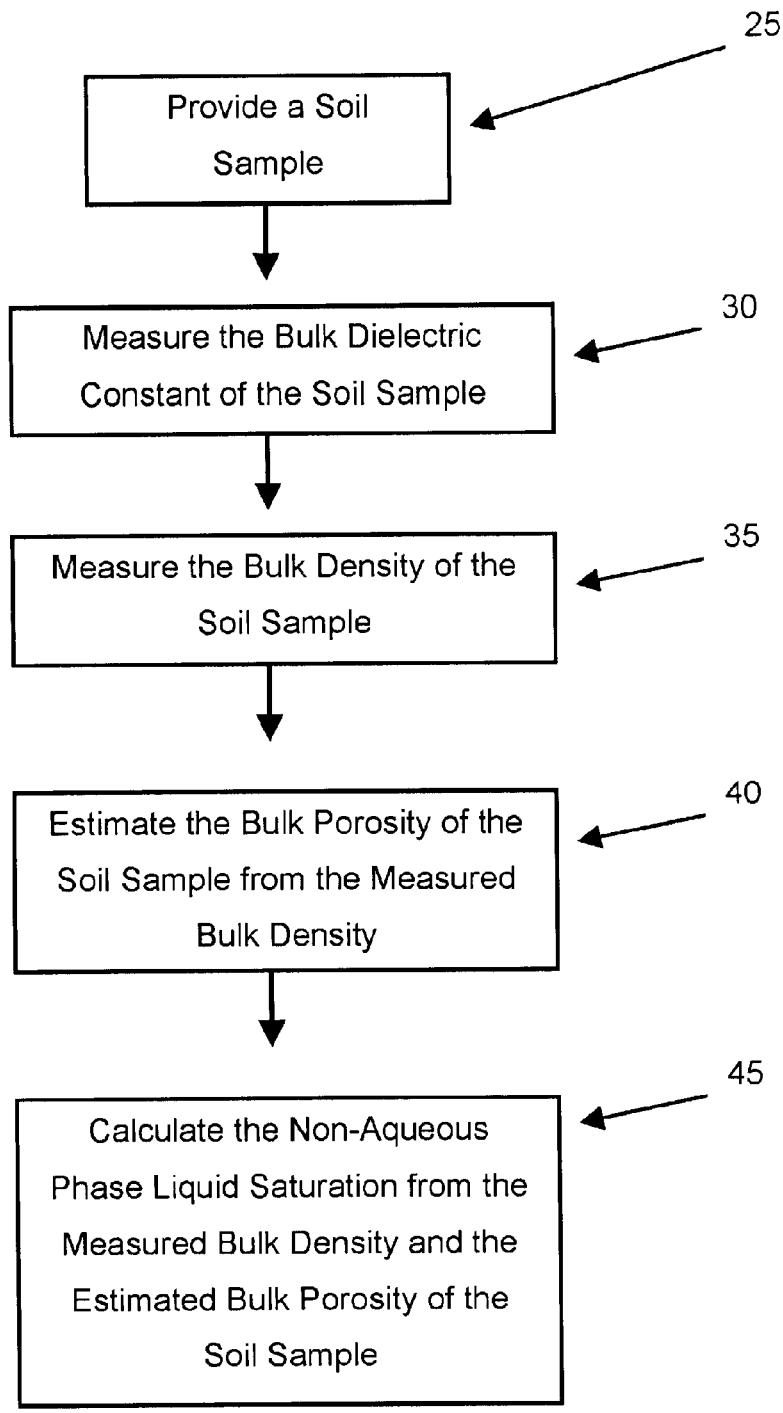
FIG. 18 is a flow diagram illustrating the method for detection and quantification of a non-aqueous phase liquid as described by the present invention.

As illustrated by the flow diagram of FIG. 18, the present invention provides a method for the detection and quantification of a non-aqueous phase liquid that includes providing a soil sample 25, measuring the bulk dielectric constant of the sample 30, measuring the bulk density of the sample 35, estimating the bulk porosity of the sample from the measured bulk density 40 and calculating the non-aqueous phase liquid saturation from the measured bulk dielectric constant and the estimated bulk porosity 45.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of detecting and quantifying non-aqueous phase liquids in a soil sample, the method comprising the steps of:

measuring the bulk dielectric constant of the sample;
   measuring the bulk density of the sample;
   estimating the bulk porosity of the sample from the measured bulk density; and
   calculating the non-aqueous phase liquid saturation from the measured bulk dielectric constant and the estimated bulk porosity.

2. The method of claim 1, wherein the step of estimating the bulk porosity of the sample from the measured bulk density assumes 100% water saturation.

3. The method of claim 1, wherein the step of estimating the bulk porosity of the sample from the measured bulk density assumes a matrix density of 2.65 g/cc.

4. The method of claim 1, wherein the non-aqueous phase liquid is a dense non-aqueous phase liquid.

5. The method of claim 1, wherein the soil sample is in a subsurface and the steps of measuring the bulk dielectric constant and measuring the bulk density are performed in situ.

6. The method of claim 5, further comprising measuring the bulk dielectric constant of the sample at a plurality of depths within the subsurface and measuring the bulk porosity of the sample at the plurality of depths.

7. The method of claim 6, wherein the bulk dielectric constant measurements at the plurality of depths and the bulk porosity measurements at the plurality of depths are used to calculate the non-aqueous phase liquid saturation at the plurality of depths.

8. A method of detecting and quantifying in situ non-aqueous phase liquids in the subsurface, the method comprising the steps of:

providing at least one logging well;

providing an active gamma logging tool;

measuring the bulk density of the subsurface at a first plurality of vertical intervals along the length of the logging well utilizing the active gamma logging tool;

providing a cone-penetrometer tool having dielectric constant measurement capability;

measuring the dielectric constant of the subsurface at a second plurality of vertical intervals utilizing the cone-penetrometer tool;

interpolating the measured bulk density at the first plurality of vertical intervals and the measured dielectric constant at the second plurality of vertical intervals to establish a plurality of consistent vertical intervals;

estimating the bulk porosity of the subsurface from the interpolated bulk density measurements, assuming 100% water saturation and a matrix density of 2.65 g/cc; and calculating the percent dense non-aqueous phase liquid saturation at the plurality of consistent vertical intervals from the interpolated dielectric constant and the interpolated bulk porosity.

9. A method of detecting and quantifying in situ non-aqueous phase liquids in the subsurface, method comprising the steps of:

providing a cone-penetrometer tool, further comprising a bulk density measurement device and a dielectric constant measurement device;

measuring the bulk density of the subsurface at a plurality of vertical intervals within the subsurface utilizing the cone penetrometer tool;

measuring the dielectric constant of the subsurface at the plurality of vertical intervals utilizing the cone-penetrometer tool;

estimating the bulk porosity of the subsurface from the measured bulk density; and calculating the percent non-aqueous phase liquid saturation at the plurality of vertical intervals from the dielectric constant and the bulk porosity.

* * * * *